US00PP33007P2

(12) United States Plant Patent
Smit

(10) Patent No.: US PP33,007 P2
(45) Date of Patent: Apr. 27, 2021

(54) ***PEPEROMIA* PLANT NAMED 'EC-PEPE-2007'**

(50) Latin Name: *Peperomia caperata*
Varietal Denomination: EC-PEPE-2007

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 16/974,074

(22) Filed: Sep. 22, 2020

(51) Int. Cl.
*A01H 6/00* (2018.01)
*A01H 5/02* (2018.01)

(52) U.S. Cl.
USPC ..... Plt./373

(58) Field of Classification Search
USPC ..... Plt./373
CPC ..... A01H 6/00; A01H 5/02
See application file for complete search history.

*Primary Examiner* — Keith O. Robinson

(57) ABSTRACT

A new cultivar of *Peperomia* plant named 'EC-PEPE-2007' that is characterized by leaves that are grey-green on the upper surface with dark grey veins, leaves that are bright red on the lower surface and a rosette like plant habit.

1 Drawing Sheet

Botanical classification: *Peperomia caperata.*
Variety denomination: 'EC-PEPE-2007'.

BACKGROUND OF THE INVENTION

The present invention relates to a new and distinct cultivar of *Peperomia* plant botanically known as *Peperomia caperata* and hereinafter referred to by the cultivar name 'EC-PEPE-2007'.

'EC-PEPE-2007' originated from the crossing of the female or seed parent, a proprietary *Peperomia caperata* cultivar identified as '15OB-87' (not patented) and the male or pollen parent, a proprietary *Peperomia caperata* cultivar identified as '15OB-78' (not patented). The crossing was conducted in 2017 in Sappemeer, Netherlands. The resulting seeds were subsequently planted and grown. The cultivar 'EC-PEPE-2007' was selected by the inventor in 2018 in a controlled environment as a single plant within the progeny of the stated cross in a cultivated area of Sappemeer, Netherlands.

Asexual reproduction of the new cultivar 'EC-PEPE-2007' first occurred by leaf cuttings in 2018 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'EC-PEPE-2007'. These traits in combination distinguish 'EC-PEPE-2007' as a new and distinct cultivar apart from other existing varieties of *Peperomia* known by the inventor.

1. *Peperomia* 'EC-PEPE-2007' exhibits leaves that are grey-green on the upper surface with dark grey veins.
2. *Peperomia* 'EC-PEPE-2007' exhibits leaves that are bright red on the lower surface.
3. *Peperomia* 'EC-PEPE-2007' exhibits a rosette like plant habit.

The closest comparison cultivars are *Peperomia* 'Eden Rosso' (U.S. Plant Pat. No. 24,379) and *Peperomia* 'Piccolo Banda' (U.S. Patent Application Publication 2018/0077840). 'EC-PEPE-2007' is distinguishable from 'Eden Rosso' by the following characteristics:

1. *Peperomia* 'EC-PEPE-2007' exhibits leaves that are grey-green on the upper surface with dark grey veins. In comparison, the leaves of 'Eden Rosso' are dark green on the upper surface.
2. *Peperomia* 'EC-PEPE-2007' exhibits leaves that are bright red on the lower surface. In comparison, the leaves of 'Eden Rosso' are darker red on the lower surface.
3. *Peperomia* 'EC-PEPE-2007' exhibits leaves that are larger in size than the leaves of 'Eden Rosso'.

'EC-PEPE-2007' is distinguishable from 'Piccolo Banda' by the following characteristics:

1. *Peperomia* 'EC-PEPE-2007' exhibits leaves that are grey-green on the upper surface with dark grey veins. In comparison, the leaves of 'Piccolo Banda' are green with brown stripes on the upper surface.
2. *Peperomia* 'EC-PEPE-2007' exhibits a larger overall plant size than the overall plant size of 'Piccolo Banda'.
3. *Peperomia* 'EC-PEPE-2007' exhibits leaves that are larger in size that the leaves of 'Piccolo Banda'.

'EC-PEPE-2007' is distinguishable from the female parent plant, by the following characteristics:

1. *Peperomia* 'EC-PEPE-2007' exhibits leaves that are bright red on the lower surface. In comparison, the leaves of the female parent plant are grey-green on the lower surface.
2. *Peperomia* 'EC-PEPE-2007' exhibits leaves that are smaller in size that the leaves of the female parent plant.

'EC-PEPE-2007' is distinguishable from the male parent plant by the following characteristics:

1. *Peperomia* 'EC-PEPE-2007' exhibits leaves that are grey-green on the upper surface with dark grey veins.

In comparison, the leaves of the male parent plant are green on the upper surface.

BRIEF DESCRIPTION OF THE DRAWING

The accompanying photograph illustrates the distinguishing traits of *Peperomia* 'EC-PEPE-2007'. The photograph shows an overall view of a 30 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'EC-PEPE-2007'. Data was collected in Sappemeer, Netherlands from 30 week old plants grown in a glass greenhouse in 13 cm. diameter containers. The time of year was Spring and the temperature range was 20-23 degrees Centigrade during the day and 18-20 degrees Centigrade at night. The light level was natural light level with a shade screen. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-PEPE-2007' has not been tested under all possible conditions and phenotypic differences may be observed with variations in environmental, climatic, and cultural conditions, however, without any variance in genotype.

Botanical classification: *Peperomia caperata* 'EC-PEPE-2007'.

Annual or perennial: Perennial.

Parentage: 'EC-PEPE-2007' is a hybrid of the female parent, *Peperomia* '15OB-87' and the male parent, *Peperomia* '15OB-78'.

Plant type: Potted plant.

Growth habit: Rosette of leaves, forming short thick stems.

Plant shape: Flattened globe shaped with inflorescences carried slightly above the foliage plane.

Suitable container size: 7 cm. pots or larger.

Plant height to top of foliage: Average 12.8 cm.

Plant height to top of floral plane: Average 15.1 cm.

Plant width: Average 23.4 cm.

Vigor: Moderate.

Growth rate: Moderate.

Low temperature tolerance: 10° Centigrade.

High temperature tolerance: 40° Centigrade.

Propagation: Leaf cuttings.

Time to initiate roots (summer): 10 days at 18 to 20° C.

Time to initiate roots (winter): 14 days at 18 to 20° C.

Time to produce a rooted cutting (summer): 80 days at 18 to 20° C.

Time to produce a rooted cutting (winter): 100 days at 18 to 20° C.

Crop time: Approximately 30 weeks in Sappemeer, Netherlands.

Root system: Herbaceous.

Plant fragrance: None.

Stem:

- *Branching habit*.—Short thick main stems branching into rosettes of leaves, no lateral branches.
- *Pinching*.—Not required.
- *Number of main stems per plant*.—Average 6.
- *Main stem dimensions*.—Average 1.8 cm. in length and 5.0 mm. in diameter.
- *Internode length*.—Average 2.5 mm.
- *Stem appearance*.—Succulent.
- *Stem shape*.—Rounded.
- *Stem texture*.—Smooth.
- *Stem luster*.—Slightly glossy.
- *Stem pubescence*.—Absent.
- *Stem angle*.—Average 15 degrees from vertical.
- *Stem strength*.—Moderately strong.
- *Stem color* (*young*).—In between 183A and N186CC.
- *Stem color* (*mature*).—200B, slightly tinged N186C.
- *Internode color*.—200B, slightly tinged N186C.

Foliage:

- *Leaf arrangement*.—Alternate.
- *Compound or single*.—Single.
- *Quantity of leaves per branch*.—Average 8.
- *Leaf shape*.—Ovate.
- *Leaf aspect*.—Strongly concave.
- *Leaf apex*.—Acute to slightly apiculate.
- *Leaf base*.—Hastate, lobes touching to overlapping.
- *Leaf dimensions*.—Average 5.8 cm. in length and 3.7 cm. in width.
- *Leaf texture upper surface*.—Glabrous, velvety, moderately to strongly leathery.
- *Leaf texture lower surface*.—Glabrous, moderately to strongly leathery.
- *Leaf luster upper surface*.—Glossy.
- *Leaf luster lower surface*.—Moderately glossy.
- *Pubescence*.—Absent (both surfaces).
- *Leaf margin*.—Entire.
- *Leaf lobed*.—Not lobed.
- *Leaf rugose*.—Not rugose (both surfaces).
- *Venation pattern*.—Parallel, strongly furrowed.
- *Young leaf color* (*upper surface*).—198A, veins 200B.
- *Young leaf color* (*lower surface*).—184B.
- *Mature leaf color* (*upper surface*).—In between N189B and N189C.
- *Mature leaf color* (*lower surface*).—181A.
- *Vein color* (*upper surface*).—N189A.
- *Vein color* (*lower surface*).—In between 183A and 200C.

Petiole:

- *Petiole dimensions*.—Average 5.1 cm. in length and 3.5 cm. in diameter.
- *Petiole texture*.—Glabrous.
- *Petiole luster*.—Moderately glossy on both sides.
- *Petiole pubescence*.—Absent.
- *Petiole strength*.—Low.
- *Petiole color*.—181A with dense fine stripes 182D.

Flower:

- *Inflorescence type*.—Axillary spike.
- *Inflorescence dimensions*.—Average 6.0 cm. in length and 3.5 mm. in diameter.
- *Quantity of flowers per inflorescence*.—Average 800 per spike.
- *Quantity of flowers per plant*.—Average 2400.
- *Quantity of buds per plant*.—Average 2400.
- *Quantity of flowers and buds per plant*.—Average 4800.
- *Fragrance*.—None.
- *Natural flowering season*.—Spring.
- *Bud length*.—Average 0.5 mm.
- *Bud diameter*.—Average 0.5 mm.
- *Bud shape*.—Flattened orbicular.

*Bud texture*.—Glabrous, smooth, moderately velvety.
*Bud luster*.—Slightly glossy.
*Bud color*.—178A.
*Flower type and form*.—Flowers consist of one bract, two stamens and one pistil, no petals or sepals present.
*Flower aspect*.—Outward.
*Flower shape*.—Rotate, one bract, two stamens and one pistil.
*Flower dimensions*.—Average 0.6 mm. in diameter, 1.0 mm. in height, 0.4 mm. in depth.
*Flower longevity*.—Approximately 1 month.
*Persistent or self-cleaning*.—Self-cleaning.

Peduncle:
*Peduncle dimensions*.—Average 14.9 cm. in length and 3.0 mm. in diameter.
*Peduncle angle*.—Average 15 degrees from vertical.
*Peduncle strength*.—Weak.
*Peduncle texture*.—Glabrous, smooth.
*Peduncle luster*.—Slightly glossy.
*Peduncle color*.—181A with moderate fine stripes 197D.

Bracts:
*Bract arrangement*.—Below each flower is a single bract.
*Bract dimensions*.—Average 4.0 mm. in length and 4.0 mm. in diameter.
*Bract shape*.—Orbicular.
*Bract color*.—178A.

Reproductive organs:
*Stamen number*.—2.
*Anther shape*.—Kidney shaped.
*Anther length*.—Average 0.2 mm.
*Anther width*.—Average 0.2 mm.
*Anther color*.—146D.
*Filament length*.—Average 0.1 mm.
*Filament color*.—147D.
*Amount of pollen*.—None.
*Number of pistils*.—1.
*Pistil length*.—Average 0.2 mm.
*Stigma shape*.—Flattened, circular.
*Stigma dimensions*.—Average 0.1 mm. in length and 0.1 mm. in diameter.
*Stigma color*.—144B.
*Style*.—Not visible.
*Ovary color*.—147D.

Fruit and seed: 'EC-PEPE-2007' has not produced fruit or seed to date.

Disease and pest resistance: Disease and pest resistance has not been observed.

The invention claimed is:

1. A new and distinct variety of *Peperomia* plant named 'EC-PEPE-2007' as described and illustrated.

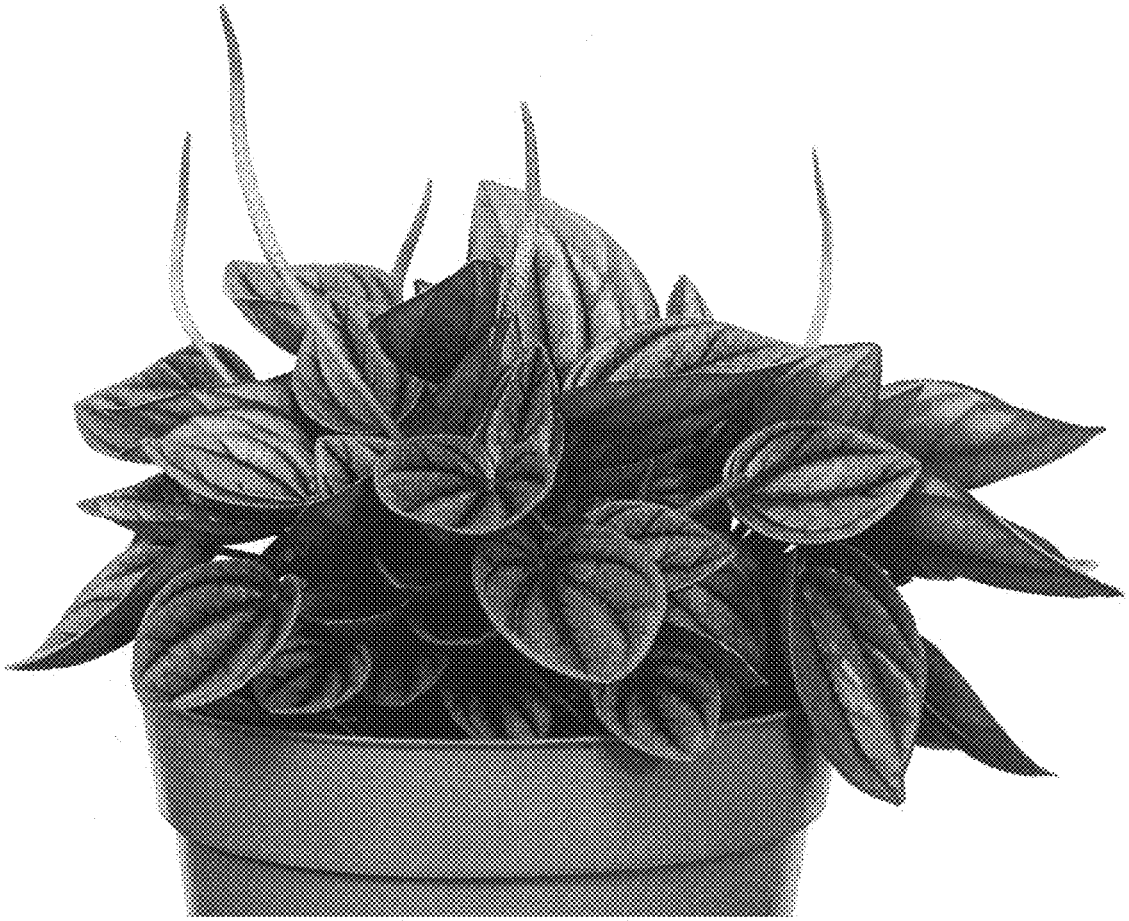

* * * * *